United States Patent [19]

Sessler et al.

[11] Patent Number: 5,955,586
[45] Date of Patent: Sep. 21, 1999

[54] HIGHLY BORONATED DERIVATIVES OF TEXAPHYRINS

[76] Inventors: Jonathan L. Sessler, 5005 Crestway Dr., Austin, Tex. 78731; William E. Allen, 9617 Great Hills Trail, #511, Austin, Tex. 78759; Vladimir A. Král, Na Kozacce 8, 12000 Praha 2, Czech Rep.

[21] Appl. No.: 08/821,272

[22] Filed: Mar. 20, 1997

Related U.S. Application Data

[60] Provisional application No. 60/013,872, Mar. 22, 1996.

[51] Int. Cl.$^6$ ........................................... C07F 5/00
[52] U.S. Cl. .................. 534/15; 424/9.3; 424/9.362; 534/10
[58] Field of Search ................... 424/1.11, 1.65, 424/1.69, 1.73, 9.1, 9.3, 9.34, 9.35, 9.361, 9.362, 9.36; 534/7, 10–16; 540/145, 465, 472, 474; 514/185, 410

[56] References Cited

U.S. PATENT DOCUMENTS

| | | | |
|---|---|---|---|
| 4,935,498 | 6/1990 | Sessler et al. | 534/15 |
| 4,959,356 | 9/1990 | Miura et al. | 514/64 |
| 5,066,479 | 11/1991 | Hawthorne | 424/1.1 |
| 5,149,801 | 9/1992 | Kahl et al. | 540/145 |
| 5,159,065 | 10/1992 | Sessler et al. | 534/15 |
| 5,252,720 | 10/1993 | Sessler et al. | 534/11 |
| 5,272,250 | 12/1993 | Spielvogel | 530/300 |
| 5,328,678 | 7/1994 | Fujii et al. | 424/1.21 |
| 5,410,045 | 4/1995 | Sessler et al. | 540/472 |
| 5,457,195 | 10/1995 | Sessler et al. | 540/472 |
| 5,489,673 | 2/1996 | Wilbur | 536/17.1 |
| 5,733,903 | 3/1998 | Sessler et al. | 514/185 |
| 5,744,302 | 4/1998 | Sessler et al. | 435/6 |

OTHER PUBLICATIONS

M.F. Hawthorne. *Angew. Chem. Int. Ed. Engl.,* 1993, 39:950.
R.F. Barth et al. *Scientific American,* 1990, Oct.:100.
M. Miura e al. *Tetrahedron Lett.,* 1990, 31:2247.
Z.J. Lesnikowski and R.F. Schinazi. *J. Org.Chem.,* 1993, 58:6531.
B.L. Iverson et al. *J. Org. Chem.,* 1995, 60:6616.
R. C. Haushalter et al. *J. Am Chem. Soc.,* 1981, 103:2620.
S.B. Kahl and M–S Koo. *J. Chem. Soc., Chem. Commun.,* 1990, 1769–1771.
L.I. Zakharkin. *Tetrahedron Lett.,* 1964, 33:2255.
T.L. Heying et al. *Inorg. Chem.,* 1963, 2:1097.
M.M. Fein et al. *Inrog. Chem.,* 1963, 2:1115.
D. Grafstein et al. *Inorg. Chem.,* 1963, 2:1120.
L.R. Huang et al. *JMRI,* 1993, 3:351.
R.C. Hausshalter and R.W. Rudolph. *J. Am. Chem. Soc.,* 1978.
J.S. Hill et al. *Proc. Natl. Acad. Sci. USA,* 1992, 89:1785.
K. Ishiwata et al. *Nucl. Med. Biol.,* 1991, 18:745.
R.F. Barth et al. *Cancer,* 1992, 70:2995.
R.G. Zamenhof et al. *J. Natl. Cancer Inst.,* 1992, 84:1290.
T. Nguyen et al. *Radiation Research,* 1993, 133:33.
G. Fulcrand–El Kattan et al. *J. Med. Chem.,* 1994, 37:2583.
G. Fulcrand–El Kattan et al. *J. Am. Chem. Soc.,* 1994, 116:7494.
S.B. Kahl and R.A. Kasar. *J. Am. Chem. Soc.,* 1996, 118:1223.
K. Woodburn, A.S. Phadke and A.R. Morgan. *Bioorganic & Med. Chem. Letters,* 3(10): 2017–2022 (1993).

*Primary Examiner*—Jose' G. Dees
*Assistant Examiner*—Dameron Jones
*Attorney, Agent, or Firm*—Jacqueline S. Larson

[57] ABSTRACT

The present invention is directed to highly boronated derivatives of expanded porphyrins including sapphyrins and texaphyrins, and more particularly to expanded porphyrins substituted with carborane clusters. Such compositions are useful in boron neutron capture therapy, radiation therapy, photodynamic therapy, and other applications.

17 Claims, No Drawings

HIGHLY BORONATED DERIVATIVES OF TEXAPHYRINS

This application is entitled to the benefit of the filing date of copending provisional application Ser. No. 60/013,872, filed on Mar. 22, 1996, the entire disclosure of which is incorporated herein by reference.

FIELD OF THE INVENTION

The present invention relates generally to expanded porphyrins, including sapphyrins and texaphyrins, and more particularly to certain boron-containing sapphyrin and texaphyrin compounds, which compositions are useful in boron neutron capture therapy, radiation therapy, photodynamic therapy, and other applications.

BACKGROUND OF THE INVENTION

A recent review article by Hawthorne (*Angew. Chem. Int. Ed. Engl.*, 1993, 32:950) describes boron neutron capture therapy for cancer (see, also, Barth et al., *Scientific American*, 1990, Oct.:100). The use of boron compounds in the treatment of cancer is based on the unique affinity of nonradioactive $^{10}$B nuclei for thermal (low-energy) neutrons to produce, by nuclear (n,α) reaction (via unstable $^{11}$B), an α-particle and a lithium-7 particle ion with a kinetic energy of 2.31 MeV. Thus, reactants of very low energy (less than 1–2 KeV) are converted to cytotoxic products of 2.31 MeV directly within the target (such as a cancerous) cell. Since the nuclear fragments produced by this fission reaction have mean free paths for reaction with tissue that are on the order of only 5 μm ($^7$Li) and 9 μm ($^4$He), or one cell diameter, destructive radiation predominates only in the immediate vicinity of cells containing significant $^{10}$B concentrations. When this event takes place at a neoplastic lesion, one has the basis for a preferential tumor treatment.

Specifically, boron neutron capture therapy (BNCT) is a binary therapy: it relies on the use of a $^{10}$B-labeled substance that localizes preferentially in or near tumor sites, and on the irradiation of said $^{10}$B-rich sites with externally generated slow neutrons. Both of these apparently are required for success. Indeed, failures in early BNCT studies were attributed to an inadequate concentration of $^{10}$B at the cancerous sites and/or a lack of selectivity in the disposition of the $^{10}$B-containing material.

In the last two decades treatment of brain tumors using BNCT has been performed in Japan using improved boron compounds and neutron irradiation techniques. Promising results have been obtained and interest in BNCT is increasing. A major problem that remains, however, in BNCT is that associated with delivering large quantities of boron to the target structure via means of an effective and convenient carrier system. It is now clear that success in the BNCT field will require that sufficient quantities of $^{10}$B be delivered to the cancer cell so as to be able to sustain lethal reactions.

It has been calculated that an effective dose of $^{10}$B in a tumor should be in the range of 5–30 ppm. Thus, a one-fold boronated compound (i.e., a mono-boron containing species) will not meet this stringent criterion for BNCT. Compounds that make use of carborane clusters, which have a high inherent boron content, should be more effective, provided, of course, that efficient and selective uptake of the boron-containing carrier molecules by cancer or other target cells can be attained. Examples of carborane clusters are the icosahedral closo-$C_2B_{10}H_{12}$ carboranes (such as 1,2-dicarba-closo-dodecaborane (o-carborane, 1a), 1,7-dicarba-closo-dodecaborane (m-carborane, 1b), and 1,12-dicarba-closo-dodecaborane (p-carborane, 1c)) as well as other carboranes of the general formula closo-$C_2B_{n-2}H_n$, where n=6 through 12, and the corresponding closo-$CB_{n-1}H_n$—carborane series.

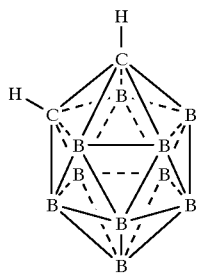

1a

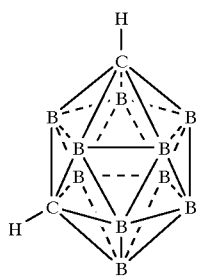

1b

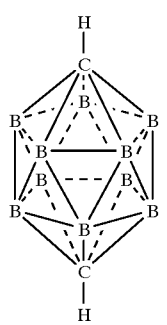

1c

Many porphyrins and porphyrinoid compounds have demonstrated an ability to selectively accumulate in tumors, and have therefore been considered as possible candidates for delivery of boron to malignant tissue (see, U.S. Pat. Nos. 4,959,356 and 5,149,801; Kahl et al., *Basic Life Sci.*, 1989, 50:325; Miura et al., *Tetrahedron Lett.*, 1990). However, no carboranyl or other boronated "expanded porphyrins" have been known or suggested.

The texaphyrins are aromatic pentadentate macrocyclic expanded porphyrins which have been found to be useful as MRI contrast agents, as radiation sensitizers and in photodynamic therapy (PDT). Texaphyrin is considered as being an aromatic benzannulene containing both 18π- and 22π-electron delocalization pathways. See, e.g., Sessler, J. L. et al., *Accounts of Chemical Research*, 1994, 27, 43. Texaphyrins and water-soluble texaphyrins and methods of preparation have been described in, for example, U.S. Pat. Nos. 4,935,498; 5,252,720; 5,256,399; 5,272,142; 5,292,414; 5,457,183; 5,583,220; and 5,599,923; all of which are incorporated herein by reference.

The sapphyrins are 22π-electron pentapyrrolic macrocyclic expanded porphyrins which are useful for PDT, as anion chelating agents, and in the separation of nucleotides and oligonucleotides. Sapphyrins and water-soluble sapphyrins and methods of preparation have been described in, for example, U.S. Pat. Nos. 5,041,078; 5,120,411; 5,159,065; 5,302,714; 5,457,195; and 5,543,514; and in PCT Publication No. WO 94/09003; all of which are incorporated herein by reference.

SUMMARY OF THE INVENTION

The present invention is directed to highly boronated derivatives of expanded porphyrins, including sapphyrins and texaphyrins. By "highly boronated derivatives" is meant that the expanded porphyrin molecule will include at least four boron atoms, and. preferably will include at least ten boron atoms. The boron atoms are preferably present in the expanded porphyrin molecule as carborane clusters, (also referred to herein as carboranyl clusters) which have a high inherent boron content. There may be one carborane cluster or more than one carborane cluster in the highly boronated expanded porphyrin derivative.

The texaphyrins are a preferred expanded porphyrin in this invention. Such compounds offer a significant advance over porphyrin-based systems because (i) they form stable 1:1 complexes with trivalent lanthanide ions, particularly Gd(III) and Lu(III), and can thus be used for delivery of boron in conjunction with magnetic resonance imaging (in the case of paramagnetic metal ions) or photodynamic cancer therapy (with diamagnetic metal ions); (ii) they possess a lower inherent toxicity; (iii) they are readily derivatized on the tripyrrole (T) and/or benzene (B) portions of the macrocycle, with, for example, water-solubilizing groups such as hydroxypropyl, poly(ethylene glycol), saccharides, oligopeptides and oligonucleotides, etc.; and (iv) they allow for the attachment of one to five or more carboranes per texaphyrin molecule.

In one embodiment of the present invention, the compounds of the invention may be characterized by the following formulas A and C.

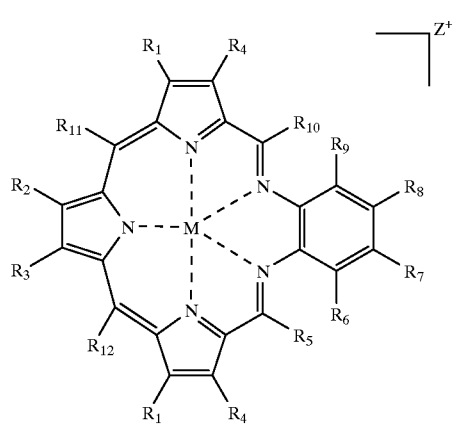

(A)

-continued

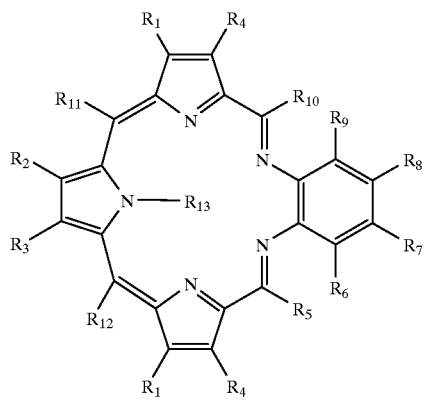

(C)

wherein M is hydrogen, a divalent metal cation or a trivalent metal cation; each of $R_1-R_4$ and $R_6-R_9$ is independently hydrogen, halide other than iodide, hydroxyl, alkyl, alkenyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, carboranyl, a catalytic group, or a site-directing molecule, with the proviso that at least one of $R_1-R_4$ and $R_6-R_9$ is carboranyl; each of $R_5$ and $R_{10}-R_{12}$ is independently hydrogen, alkyl, alkenyl, aryl, hydroxyalkyl, oxyalkyl, oxyhydroxyalkyl, aminoalkyl, oxyaminoalkyl, carboxyalkyl, or carboxyamidealkyl; $R_{13}$ is alkyl, alkenyl, oxyalkyl or hydroxyalkyl having up to about three carbon atoms and having rotational flexibility around a first-bound carbon atom; and Z is zero or an integer less than or equal to 5.

In another embodiment, the compounds of the present invention are characterized by the following formula B:

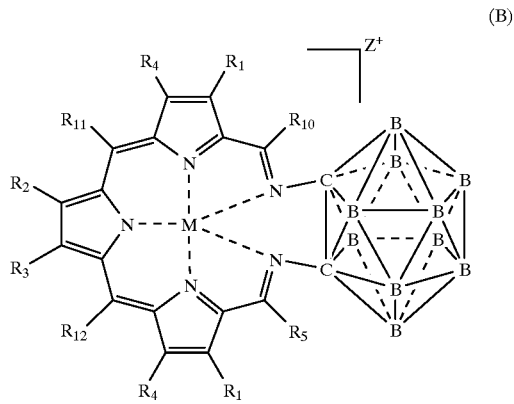

(B)

wherein, M is hydrogen, a divalent metal cation or a trivalent metal cation; each of $R_1-R_4$ is independently hydrogen, halide other than iodide, hydroxyl, alkyl, alkenyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, carboranyl, a catalytic group, or a site-directing molecule; each of $R_5$ and $R_{10}-R_{12}$ is independently hydrogen, alkyl, alkenyl, aryl, hydroxyalkyl, oxyalkyl, oxyhydroxyalkyl, aminoalkyl, oxyaminoalkyl, carboxyalkyl, or carboxyamidealkyl; and Z is 0, 1 or 2.

The invention further includes the use of highly boronated expanded porphyrins, including sapphyrin and texaphyrin, in boron neutron capture therapy for cancer.

DETAILED DESCRIPTION OF THE INVENTION AND PREFERRED EMBODIMENTS

To illustrate how multiple boron atoms may be attached to the texaphyrin core to make the derivatives of formula A or C, thus making this class of molecules useful within the context of BNCT, two synthetic strategies for the introduction of boron have been developed. Both are based on the preparation of carborane-substituted texaphyrins since, as would be appreciated by one skilled in the art, the use of carborane derivatives allows the attachment of multiple boron atoms onto a chosen molecular skeleton.

The first strategy involves formation of an ester bond between an activated carborane carboxylic acid and a hydroxylated texaphyrin, such as those disclosed in the patents previously incorporated herein by reference, via three different coupling methods, namely those involving the use (1) of an acid chloride, (2) of carbodiimide-induced dehydration, and (3) of 1,1'-carbonyldiimidazole-mediated activation. Dry 1,2-dichloroethane, DMF, or dichloromethane were used as the solvents. Pyridine was used as a base and 4-dimethylaminopyridine was chosen as the catalyst. Yields were on the order of 35–75% and the ester-containing products were in all cases stable to acid. Following these procedures, carboranes could be appended to one, to some or to all of the hydroxyl groups of a texaphyrin.

The carborane carboxylic acid and acid chloride may be prepared according to the following method:

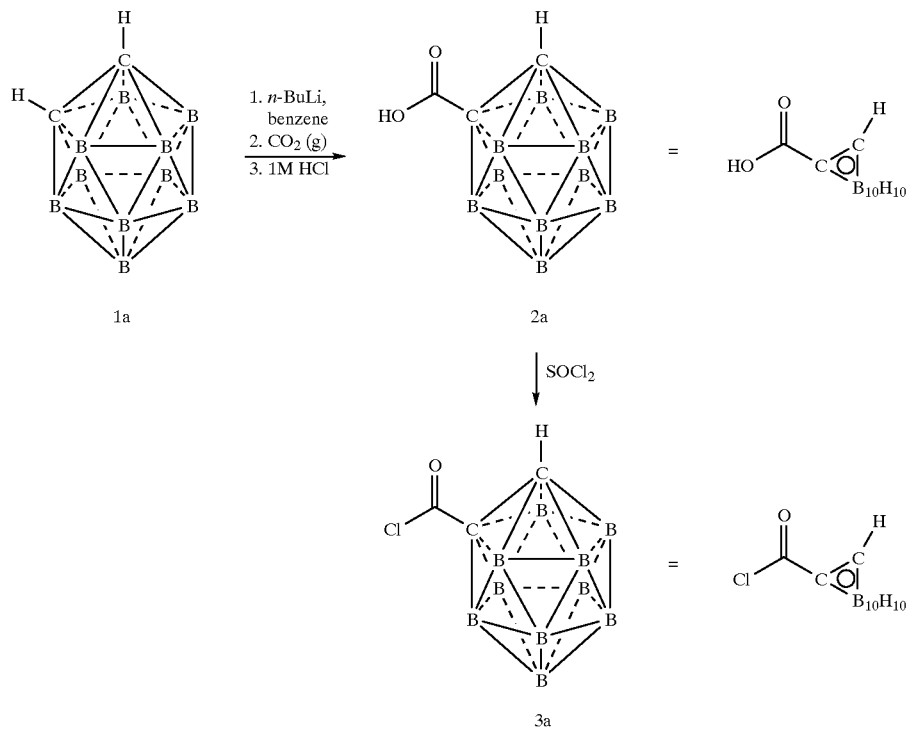

Alternatively, and preferably, the carborane carboxylic acid may be prepared according to the following method, which is a modification of the procedure in JOC, 1993, 58:6531–6534. The decaborane $B_{10}H_{14}$ is commercially available.

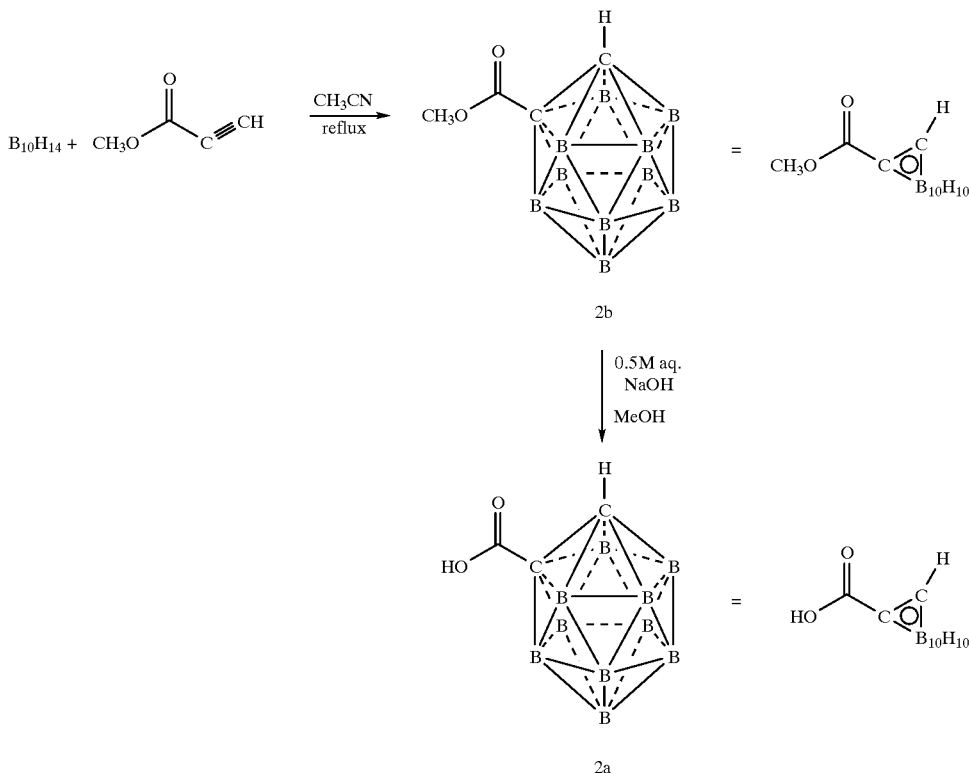

In the second synthetic approach, carborane moieties are attached to appropriate tripyrranes or benzenes prior to cyclization (via the formation of, e.g., an ester bond between a carborane carboxylic acid and a hydroxy group on the tripyrrane or the benzene, as described previously herein) to form the texaphyrin macrocycles. For example, the bis(carboranyl) tripyrrane building block 4 is used for the synthesis of reduced sp$^3$ texaphyrin intermediates and final sp$^2$-type metallotexaphyrins via the standard texaphyrin-forming procedures described in the U.S. Patents previously incorporated herein by reference to give texaphyrin-carborane conjugates of formula A with carboranyl derivatives at the $R_4$ position.

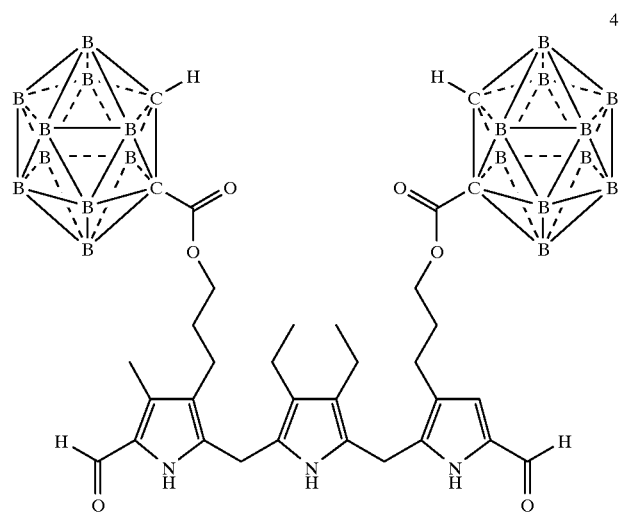

Likewise, the carboranyl dinitrobenzene 9 is reduced to the corresponding diamine and incorporated into the reduced sp$^3$ texaphyrin intermediates and final sp$^2$-type metallotexaphyrins via the standard texaphyrin-forming procedures described in the U.S. Patents previously incorporated herein by reference to give texaphyrin-carborane conjugates of formula A with carboranyl derivatives at the $R_8$ position.

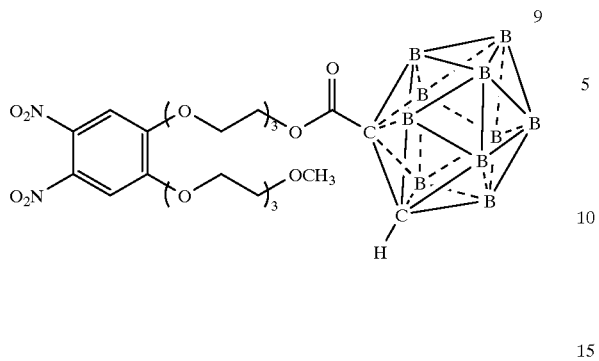

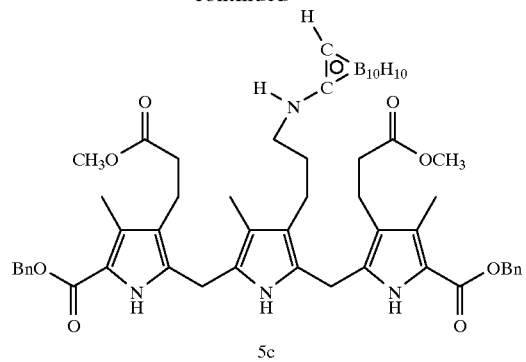

Carboranes may be attached to tripyrranes or benzenes by other methods. In particular, amino-substituted carboranes will be used to effect nucleophilic displacement of the halide ion(s) from haloalkyl-substituted tripyrranes or benzenes. For example, the halogen-bearing tripyrranes may be prepared by reaction of bis(haloalkyl)dipyrromethanes and acetoxymethylpyrroles in an addition-fragmentation reaction that is similar to one described in the general chemical literature (Iverson et al., *J. Org. Chem.*, 1995, 60:6616–6620). Using this approach, a key intermediate monobromo tripyrrane 5a was prepared by reaction of dibromo dipyrromethane and benzyl 3-methyl-5-acetoxymethyl-4-[2'-(methoxycarbonyl)ethyl]pyrrole-2-carboxylate in methanol containing trifluoroacetic acid and p-toluenesulfonic acid. Reaction of this bromide 5a with 1-amino-1,2-dicarba-closo-dodecarborane 5b should give the corresponding monocarboranyl tripyrrane 5c, followed by standard texaphyrin-forming protocols to yield the texaphyrin-monocarborane conjugate where the carborane is attached at the $R_2$ position on the texaphyrin ring. One method of synthesizing the carborane 5b is described in JACS, 1996, 1:1223–1224.

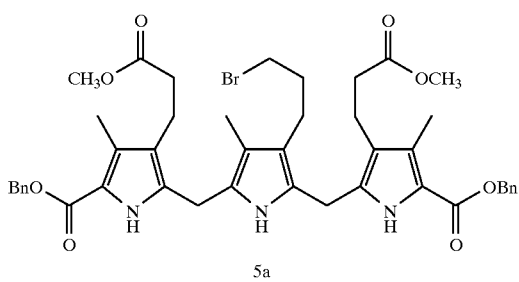

5a

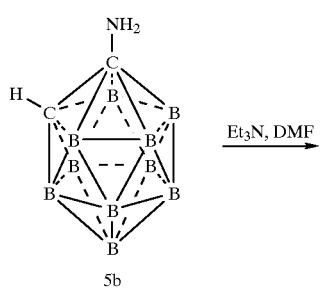

5b

Another method of attaching a carborane to a tripyrrane is as follows: The monobromo tripyrrane 5a is reacted with sodium acetylene in DMF to give the tripyrrane 5d, which is then reacted with decaborane to give the corresponding monocarboranyl tripyrrane 5e. The tripyrrane 5e is then used in the standard preparation of texaphyrins to give the corresponding texaphyrin-monocarborane conjugate where the carborane is attached at the $R_2$ position on the texaphyrin ring. Analogously, carboranyl benzenes may be produced.

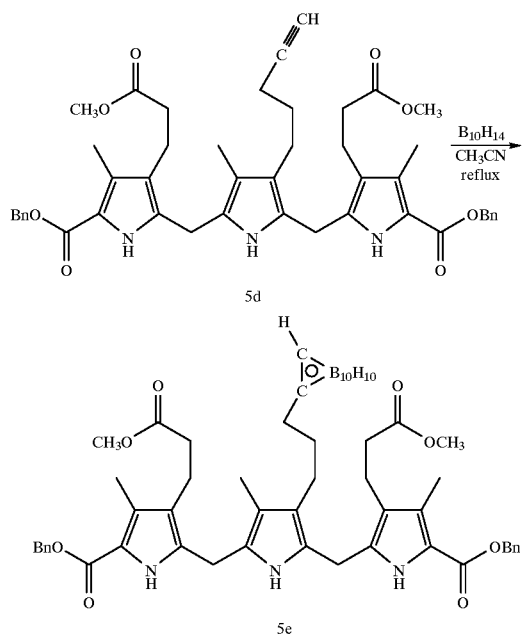

The introduction of lipophilic carborane clusters or cages to the periphery of the texaphyrin skeleton reduces the water solubility of the metal complexes by a significant margin. This problem was solved by degrading the carborane cages under basic conditions. Here, the standard approach involves heating the boronated-porphyrin compound at reflux in MeOH containing KOH as the base; (c.f.: Miura et al., *Tetrahedron Lett.*, 1990, 2247–2250). In the context of the present invention, however, this solution was non-obvious since texaphyrins are known to be unstable under basic conditions. Thus, conditions were sought under which the requisite base-mediated carborane degradation could be effected without harming the texaphyrin system in the process. After considerable experimentation it was found that reaction of a carborane-texaphyrin conjugate in a mixture of piperidine-pyridine (1:4, v:v) at room temperature (RT) for 30 h (an analogous approach was used in the porphyrin series by Haushalter et al., c.f.: *J. Am. Chem. Soc.*, 1981, 103:2620–2627), or with piperidine in DMF at 50° C. for 8 h, would work. Both sets of conditions gave the desired water-soluble texaphyrin derivatives bearing the key anionic o-nido-carborane [$C_2B_9H_{11}$]- substituents on their periphery (isolated as the piperidinium salts). Further, they both did so without effecting degradation of the texaphyrin molecule (as determined by UV/Vis spectroscopy).

To prepare the texaphyrin carborane derivatives of formula B, 1,2-diaminocarborane (6c) is used in place of 1,2-diaminobenzene to react with a tripyrrane following the standard texaphyrin synthesis route as disclosed in the U.S. Patents previously incorporated by reference herein. The 1,2-diaminocarborane may be prepared in the following manner:

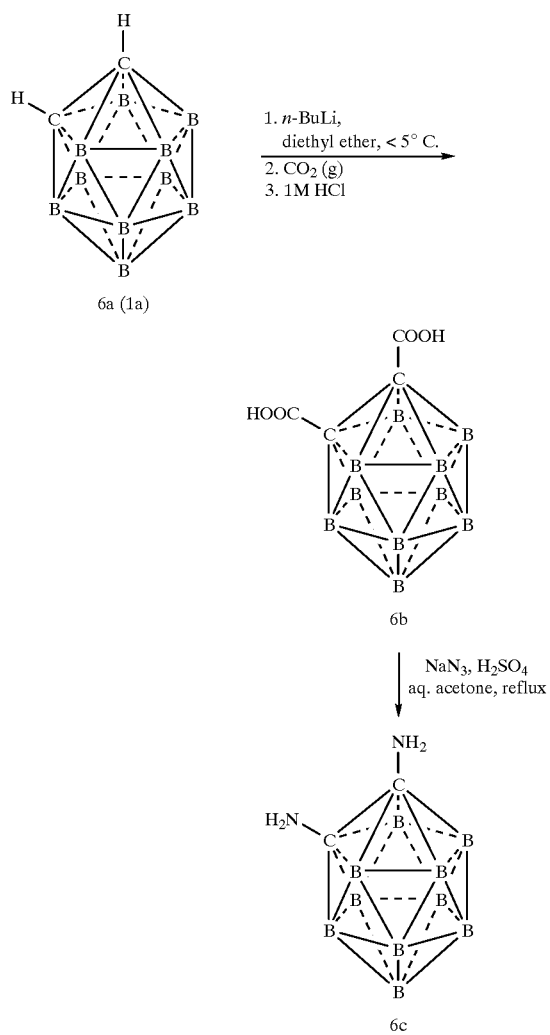

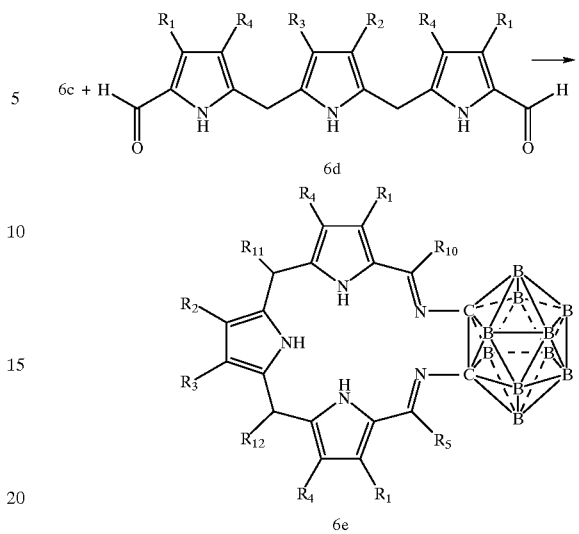

Then, following standard procedures, the diaminocarborane 6c is reacted with a diformyltripyrrole 6d via condensation to give the nonaromatic sp³ macrocycle 6e, which is then mixed together with a metal cation M, a Brønsted base and an oxidant to give, via a metallation/oxidation reaction, the final texaphyrin carborane derivative of formula B.

Additional carboranyls at the $R_1$–$R_4$ positions may be added to compound B following the procedures previously described herein.

o-Carborane diacid 6b or the corresponding 1,7- or 1,12-diacid carborane may be used to prepare carborane-spanned texaphyrin dimers under convenient conditions. Such dimers might have inherently higher localization for neoplastic sites. Alternatively, when these dimers are used as their Gd(III) or Lu(III) adducts, they might allow texaphyrin-induced enhanced magnetic resonance imaging (MRI) and photodynamic therapy (PDT), respectively, to be carried out more efficiently in conjunction with boron-based neutron capture therapy.

In the compounds of the present invention, Z will typically be zero or an integer less than or equal to 5. In the context of the basic macrocycle with a divalent or trivalent metal cation, Z is 1 or 2; however, one skilled in the art in light of the present disclosure would realize that the complexes described in the present invention may have one or more additional ligands providing charge neutralization and/or coordinative saturation to the metal ion. Such ligands include chloride, nitrate, acetate, and hydroxide, among others. The value of Z would also be altered due to charges present on, for example, a covalently attached site-directing molecule, such as charges of the phosphate groups on an oligonucleotide.

M is preferably a divalent or trivalent metal cation. The divalent metal cation may be selected from, but is not limited to, the group consisting of Ca(II), Mn(II), Co(II), Ni(II), Zn(II), Cd(II), Hg(II), Fe(II), Sm(II) and $UO_2$(II). The trivalent metal cation may be selected from, but is not limited to, the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

The pyrrole nitrogen substituent ($R_{13}$) of the texaphyrins of structure C may be an alkyl, alkenyl, hydroxyalkyl, or alkoxy group having up to about 3 carbon atoms; with the provision that the substituent has rotational flexibility after the first-bound carbon to allow the rest of the group to be positioned outside the plane of the texaphyrin. Thus, a preferred alkenyl is —$CH_2CH{=}CH_2$. The pyrrole nitrogen substituent is most preferably a methyl group.

In the invention, the following terms have the following meanings.

"Alkyl" means alkyl groups, straight, branched or as cyclic isomers, with generally one to fifty, preferably one to thirty, more preferably one to ten, carbon atoms. Presently preferred are methyl, ethyl, and propyl.

"Alkenyl" means alkenyl groups, straight, branched or as cyclic isomers, with generally two to fifty, preferably two to thirty, more preferably two to ten, carbon atoms, and with one to five or more double bonds, preferably one to five, more preferably one to three double bonds. Ethenyl and propenyl are presently preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$alkyls being preferred, and diols of $C_{1-3}$alkyls being more preferred; and polyethylene glycol, polypropylene glycol and polybutylene glycol as well as polyalkylene glycols containing combinations of ethylene, propylene and butylene.

"Oxyalkyl" means alkyl groups as herein described with oxygen atoms, including ether or ester linkages. The number of repeating oxyalkyls within a substituent may be up to 200, preferably from 1 to 20, more preferably from 1 to 7, and most preferably is 2–5. A presently preferred oxyalkyl is $O(CH_2CH_2O)_xCH_3$, where x=1–100, preferably 1–10, and more preferably, 2–5.

"Oxyhydroxyalkyl" means alkyl groups as described herein having ether or ester linkages, as well as hydroxyl groups, substituted hydroxyl groups, carboxyl groups, substituted carboxyl groups or the like.

"Alkoxycarbonyl" refers to a —$(CH_2)_n$—O—C(O)— group where n=1 to 10 or more.

"Carboxy" groups include carboxylic acids of the alkyls described herein as well as aryl carboxylic acids such as benzoic acid. "Carboxyalkyl" means alkyl groups having hydroxyl groups, carboxyl or amide substituted ethers, ester linkages, tertiary amide linkages removed from the ether, or the like. Representative examples of "carboxyamides" include primary carboxyamides ($CONH_2$), and secondary (CONHR') and tertiary (CONR'R") carboxyamides where each of R' and R" is a functional group as described herein. "Carboxyamidealkyl" means alkyl groups with hydroxyl groups, secondary or tertiary amide linkages or the like.

Representatives of useful amines include a primary, secondary, or tertiary amine of an alkyl as described hereinabove.

"Aryl" may be a compound whoses molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, unsubstituted or substituted with one ore more nitro, carboxy, sulfonic acid, hydroxy, oxyalkyl, or halide substituents.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of various sugars, and the like. Examples of amine-derivatized sugars are galactosamine, glucosamine, and sialic acid.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to ((2n+1)−2x). The hydroxyalkoxy or saccharide may be $C_nH_{((2n+1)-q)}O_yRa_q$, $OC_nH_{((2n+1)-q)}O_yRa_q$ or $(CH_2)_nCO_2Ra$ where n is a positive integer from 1 to 10,y is zero or a positive integer less than ((2n+1)−q), q is zero or a positive integer less than or equal to 2n+1, and Ra is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zRb_r$ where m is a positive integer from 1 to 10,z is zero or a positive integer less than ((2m+1)−r), r is zero or a positive integer less than or equal to 2m+1, and Rb is independently H, alkyl, hydroxyalkyl, or saccharide.

Carboxyamidealkyl may be alkyl having secondary or tertiary amide linkages or $(CH_2)_nCONHRa$, $O(CH_2)_nCONHRa$, $(CH_2)_nCON(Ra)_2$, or $O(CH_2)_nCON(Ra)_2$ where n is a positive integer from 1 to 10, and Ra is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directing molecule or catalytic group. In this case, m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zRb_r$. In this case, m is a positive integer from 1 to 10, z is zero or a positive integer less than ((2m+1)−r), r is zero or a positive integer less than or equal to 2m+1, and Rb is independently H, alkyl, hydroxyalkyl, or saccharide. In a preferred embodiment, Ra is an oligonucleotide.

Carboxyalkyl may be alkyl having a carboxyl substituted ether, an amide substituted ether or a tertiary amide removed from an ether or $C_nH_{((2n+1)-q)}O_yRc_q$ or $OC_nH_{((2n+1)-q)}O_yRc_q$ where n is a positive integer from 1 to 10; y is zero or a positive integer less than ((2n+1)−q), q is zero or a positive integer less than or equal to 2n+1, and Rc is $(CH_2)_nCO_2Rd$, $(CH_2)_nCONHRd$, $(CH_2)_nCON(Rd)_2$ or a site-directing molecule or catalytic group. In this case, n is a positive integer from 1 to 10, Rd is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to ((2m+1)−2w), and R is H, alkyl, hydroxyalkyl, or $C_mH_{((2m+1)-r)}O_zRb_r$. In this case, m is a positive integer from 1 to 10, z is zero or a positive integer less than ((2m+1)−r), r is zero or a positive integer less than or equal to 2m+1, and Rb is independently H, alkyl, hydroxyalkyl, or saccharide. In a preferred embodiment, Rc is an oligonucleotide.

The term "carboranyl", as used herein, refers to a carboranyl cluster either attached directly to the texaphyrin molecule or attached to the texaphyrin molecule by an alkyl, an alkenyl, an oxyalkyl, a carboxy, a carboxyalkyl, an oxyhydroxyalkyl, an alkoxycarbonyl, an alkylamino or other linking moiety. Examples of carboranyl clusters include those of the general formula closo-$C_2B_{n-2}H_{n-1}$, where n=6 through 12, the corresponding closo-$CB_{n-1}H_{n-1}$-carboranyl series, and the corresponding nido-carboranyl series. Specific examples of carboranyl clusters include o-carboranyl (1a'), m-carboranyl (1b'), p-carboranyl (1c'), and the o-nido-carboranyl $[C_2B_9H_{11}]$- (1d').

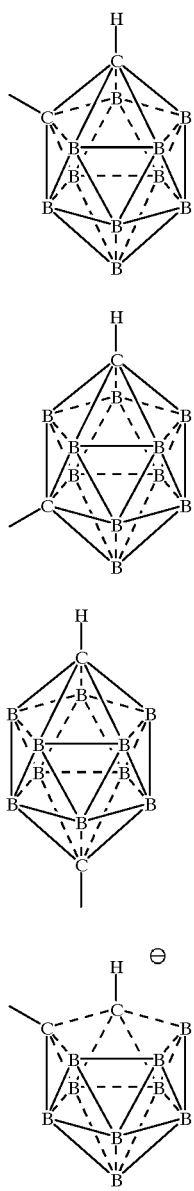

1a'

1b'

1c'

1d'

Examples of "carboranyl" groups comprising a carboranyl cluster and a linking moiety include but are not limited to the following (where "CC"=carboranyl cluster, n=0 to 10 or more, and x=1 to 200): —(CH$_2$)$_n$—O—C(O)—"CC"; —O—(CH$_2$)$_n$—"CC"; —(CH$_2$)$_n$—NH—"CC"; —O(CH$_2$CH$_2$O)$_x$—O—C(O)—"CC"; —CH=CH—(CH$_2$)$_n$—"CC".

The term "catalytic group" means a chemical functional group that assists catalysis by acting as a general acid, Brønsted acid, general base, Brønsted base, nucleophile, or any other means by which the activation barrier to reaction is lowered or the ground state energy of the substrate is increased. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, (LysAla)$_n$, (LysLeuAla)$_n$ where n is from 1–30 or preferably 1–10 or more preferably 2–7 and the like; derivatives thereof; and metallotexaphrin complexes. The term "appended to the texaphyrin complex-site directed molecule conjugate" means that the catalytic groups are attached either directly to the metallotexaphyrin complex or to the texaphyrin complex via a linker or couple of variable length, or are attached to the site-directing molecule portion of a texaphyrin complex-conjugate either with or without a linker or couple of variable length.

Exemplary site-directing molecules useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins.

The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides, deoxyribonucleotide analogs and ribonucleotide analogs are contemplated as site-directing molecules in the present invention.

The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing molecule may be attached either directly to the texaphyrin or to the texaphyrin via a linker or a couple of variable length. During catalysis, for example, the texaphyrin portion of a texaphyrin-oligonucleotide conjugate is placed in the vicinity of the substrate upon binding of the oligonucelotide to the targeted nucleic acid substrate.

A conjugate group having site specificity or catalytic activity may be covalently coupled to a texaphyrin directly on the macrocycle ring or through various couples. A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds.

In preferred embodiments, conjugates and appended groups are covalently bonded to the texaphyrin via a carbon-carbon, a carbon-nitrogen, a carbon-sulfur, or a carbon-oxygen bond, more preferred being a carbon-oxygen or a carbon-nitrogen bond.

The following examples are provided to illustrate the practice of the present invention, and are intended neither to define nor to limit the scope of the invention in any manner. In the following examples, "RT" is room temperature.

EXAMPLES 1–6

Preparation of Texaphyrin-Carborane Esters o-Carborane moieties were introduced into Gd-T2B2 (7a) or M-T2BET [8a, M=Gd(III) or Lu(III)] texaphyrins by forming ester linkages between the hydroxy groups on the texaphyrin periphery and o-carborane carboxylic acid 2a. As mentioned above, this latter species was activated prior to reaction using several different activating/dehydrating agents including dicyclohexylcarbodiimide, EDC, diisopropylcarbodiimide, and 1,1'-carbonyldiimidazole, with other such species presumably also being amenable for use in the hands of one skilled in the art of organic synthesis. Alternatively, the starting o-carborane carboxylic acid was converted into its acid chloride form 3a and reacted as such.

Synthesis of the needed starting material 1,2-dicarba-closo-dodecaborane carboxylic acid, 2a, was based on the coupling of Li salts of o-carborane 1a with carbon dioxide followed by acid workup of the reaction mixture. In our hands, in spite of references in the literature to the contrary [(a) Fein et al., *Inorg.Chem.*, 1963, 2:1115–1119; (b) Grafstein et al., *Inorg. Chem.*, 1963, 2:1120–1125; (c) Zakharkin, L. I., *Tetrahedron Lett.*, 1964, 2255–2258; (d) Heying et al., *Inorg. Chem.*, 1963, 2:1097–1105)], this approach led to the formation of a mixture of mono- and disubstituted products: 1,2-dicarba-closo-dodecaborane-carboxylic acid 2a and 1,2-dicarba-closo-dodecaborane-dicarboxylic acid. Alternatively, the monoacid 2a was prepared by the decaborane/alkyne cyclization described previously herein, and characterized via $^1$H and $^{11}$B NMR spectroscopy and low and high resolution mass spectrometry (abbreviated as LR MS and HR MS, respectively).

EXAMPLES 1–3 o-Carborane Gd-T2B2 Derivative, 7b.

The gadolinium(III) complex of the T2B2 texaphyrin derivative 7a was used as the starting material in these examples.

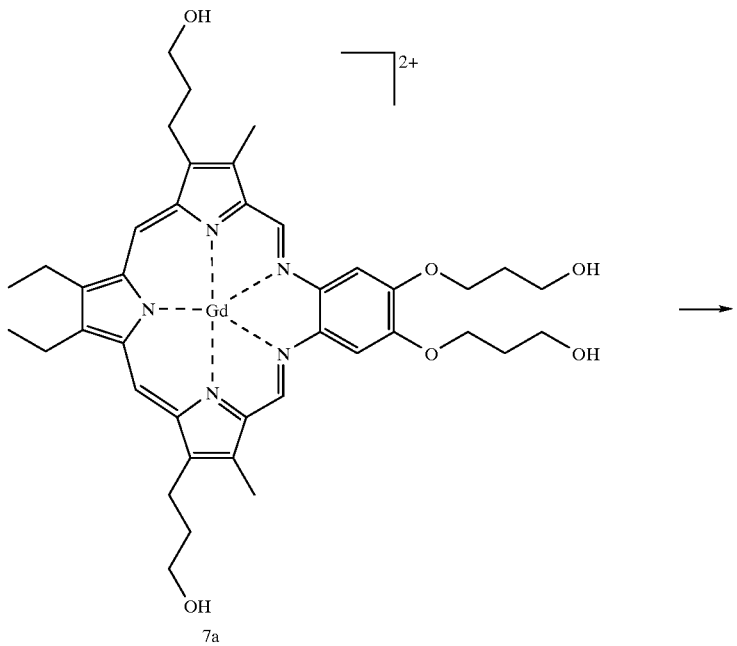

7a

-continued

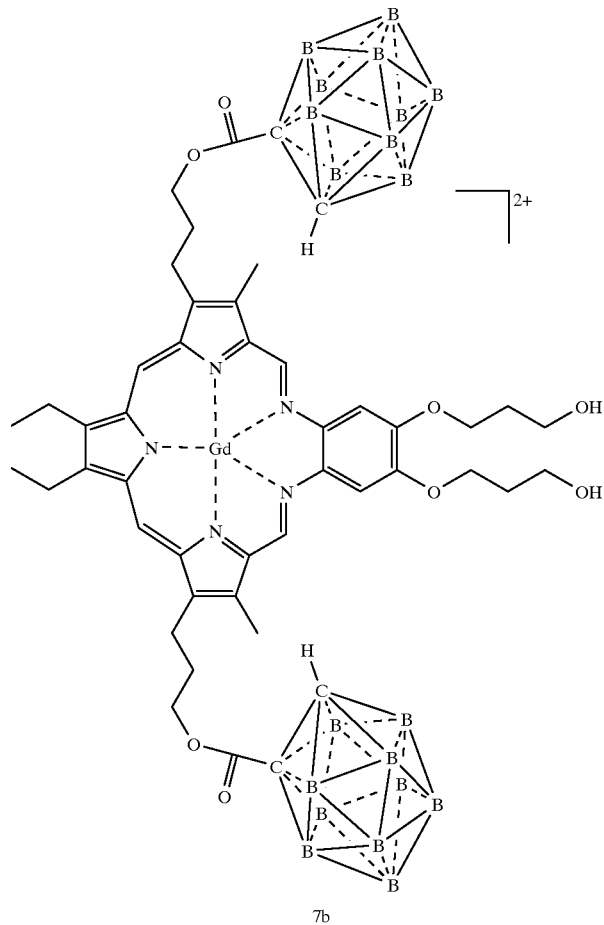

7b

EXAMPLE 1

The gadolinium(III) T2B2 derivative 7a (1 mmol) was dissolved in 10 mL of dry 1,2-dichloroethane. Pyridine (1.0 mL) was then added, together with 4-dimethylaminopyridine (20 mg). To the resulting solution was added slowly (i.e., over the course of 1 h) at RT with stirring under an argon atmosphere a solution of 2.0 mmol of the o-carborane acid chloride 3a in dry dichloromethane (10 mL) (prepared from 2.2 mmol o-carborane carboxylic acid 2a and thionyl chloride, in accord with the procedure of Heying et al., *Inorg. Chem.*, 1963, 2:1097–1105). Stirring under the inert atmosphere was continued for 40 h at RT. At this point, the solvent was removed using a rotary evaporator. The resulting residue was subject to column chromatography on neutral alumina using first dichloromethane and then dichloromethane-methanol (10:1, v:v) as the eluents. The major fraction was the desired bis(carborane) derivative 7b (50.0% yield). $^{11}$B NMR (160 MHz, CDCl$_3$ with 10% CD$_3$OD, external standard B(OCH$_3$)$_3$ is 0.0 ppm, $^1$H-decoupled): −26.5, −27.5, −29.1, −31.2, −31.9, −50.5, −53.6. LR MS (FAB, positive ion mode, nitrobenzylalcohol (NBA) matrix). Calcd. for C$_{46}$H$_{70}$B$_{20}$N$_5$O$_8$Gd: 1198.63; found 1202, 1203, 1204.

EXAMPLE 2 o-Carborane carboxylic acid 2a (0.1 mmol) was activated with diisopropylcarbodiimide (0.3 mmol) at 0° C. under standard conditions (1 h, 0° C., 1-hydroxybenzotriazole (5 mg) as a catalyst) using dry dichloromethane (20 mL) as the solvent. This activated acid was then added at 0° C. to a solution of Gd-T2B2 7a(0.1 mmol) in 20 mL of dry 1,2-dichloroethane. The resulting reaction mixture was kept for the first 1 h at 0° C. and then for 48 h at RT under nitrogen. The reaction was worked up as described above to give the bis product 7b in 43% isolated yield.

EXAMPLE 3

As an alternative to the procedure in Example 2, 1,1'-carbonyldiimidazole (3 mol eqv.) was used as the activating agent (RT for 2 h, dry 1,2-dichloroethane). The reaction was then performed on a 0.1 mmol scale in dry 1,2-dichloroethane at 60° C. for 24 h under nitrogen. In this instance the yield of purified product 7b was 41%.

EXAMPLES 4–6 o-Carborane M-T2BET Derivatives, 8b (M=Gd, Lu)

The gadolinium(III) and lutetium(m) complexes of the T2BET texaphyrin derivative were used as starting materials in this example.

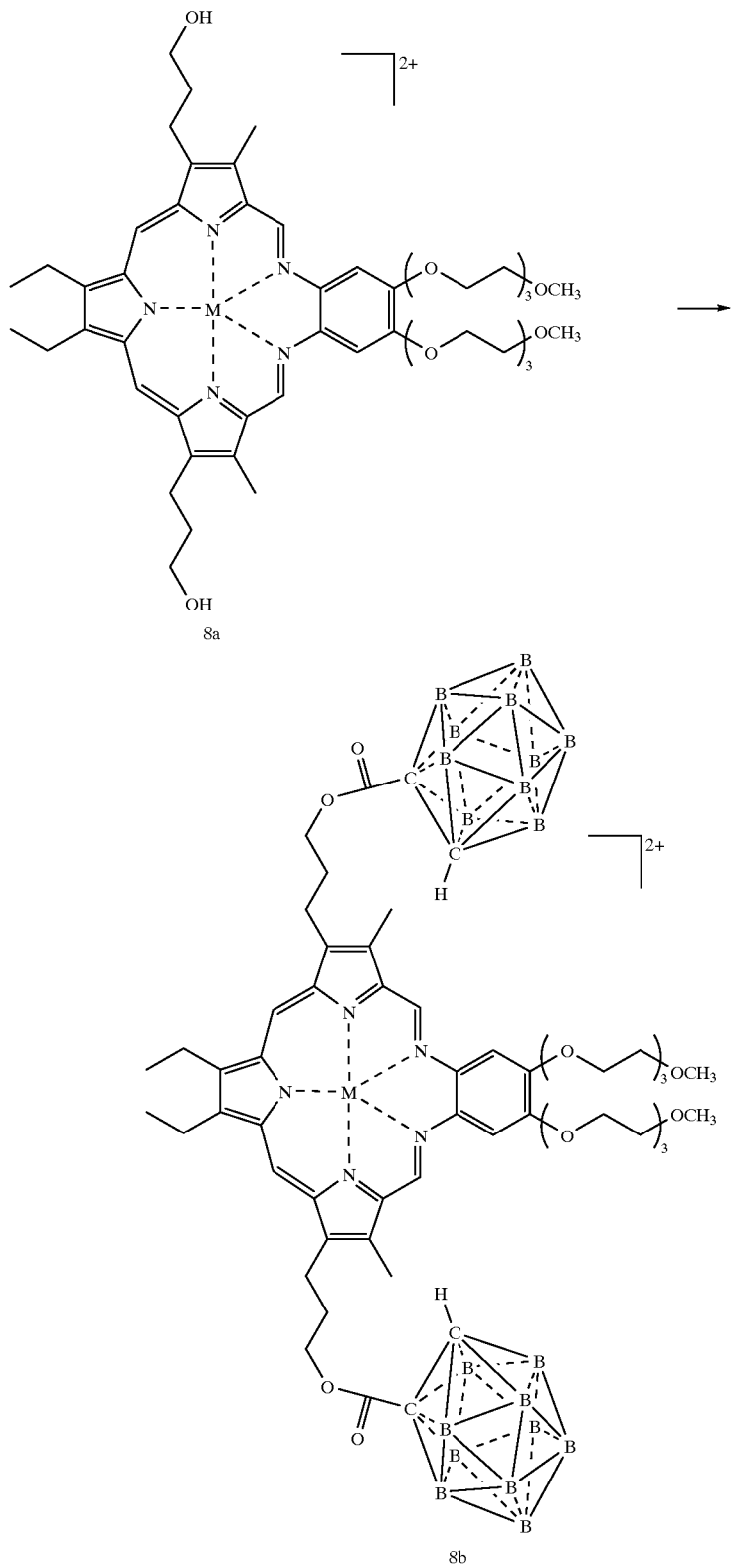
EXAMPLE 4
Gd-T2BET texaphyrin 8a (0.1 mmol; M=Gd(III)) was dissolved in 15 mL of dry dichloromethane. Dry pyridine (0.5 mL) was added together with 4-dimethylaminopyridine (10 mg). To this solution was slowly added at RT under argon the o-carborane acid chloride 3a (0.3 mmol) in dry dichloromethane (10 mL). The reaction mixture was stirred under argon at RT for 3 days. The solvent was then evaporated off in vacuo and the product purified via column chromatography using neutral alumina as the solid phase and dichloromethane-methanol (gradient from 0 to 15% of methanol) as the eluent. The yield of product 8b (M=Gd(III) is 68%. $^{11}$B NMR (160 MHz, CDCl$_3$ with 10% CD$_3$OD, external standard B(OCH$_3$)$_3$, $^1$H-decoupled): −20.2, −28.0, −28.8, −31.5, −35.1, −37.0, −39.2, −41.3, −50.2, −53.3, −55.1. LR MS (FAB, NBA matrix): Calcd. for C$_{54}$H$_{86}$B$_{20}$N$_5$O$_{12}$Gd: 1374.74; found 1372, 1373, 1374.

EXAMPLE 5

Compound 8b [M=Gd(III)] was also prepared in 55% yield using diisopropylcarbodiimide activation as described in Example 2.

EXAMPLE 6

Lu-T2BET 8a [M=Lu(III)] was converted to its corresponding bis o-closo-carborane derivative via the acid chloride route described in Example 4. This gave product 8b (M=Lu(III)) in 35% yield. LR MS (FAB, NBA matrix). Calcd. for C$_{54}$H$_{86}$B$_{20}$N$_5$O$_{12}$Lu 1391.755; found 1393, 1394.

EXAMPLE 7 o-Carborane Gd-T2B2 Derivative, 7b

This example illustrates an alternative synthetic route for the preparation of texaphyrin-carborane compounds.

Using an ester-forming coupling reaction like those described previously herein, the bis(carboranyl) tripyrrane 2,5-bis[(2-formyl-3-[3'-(o-carboranyloxy)propyl]-4-methylpyrrol-2-yl) methyl]-3,4-diethylpyrrole (4) was prepared from 1 eqv. of the corresponding dihydroxy derivative (prepared as described in the U.S. patents previously incorporated by reference herein) by treatment with 2.2 eqv. of activated o-carborane carboxylic acid 2a (activated as acid chloride 3a, or via use of diisopropylcarbodiimide) and was obtained in 65% yield following column chromatographic purification.

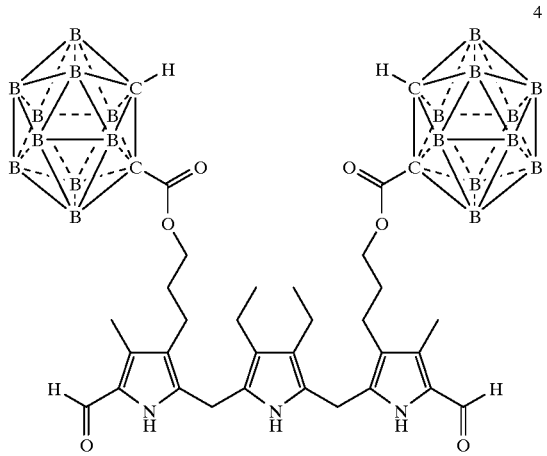

The resulting bis(carboranyl) tripyrrane 4 is then reacted with 1,2-diamino-4,5-di(3-hydroxypropyloxy)benzene (prepared as described in the U.S. patents previously incorporated by reference herein) to give a nonaromatic sp$^3$ macrocycle 10, which is then oxidized and metallated with gadolinium salt, according to standard texaphyrin synthesis procedures known in the art and disclosed in the U.S. patents previously incorporated by reference herein, to give the Gd(III) bis(carboranyl)T2B2 texaphyrin 7b.

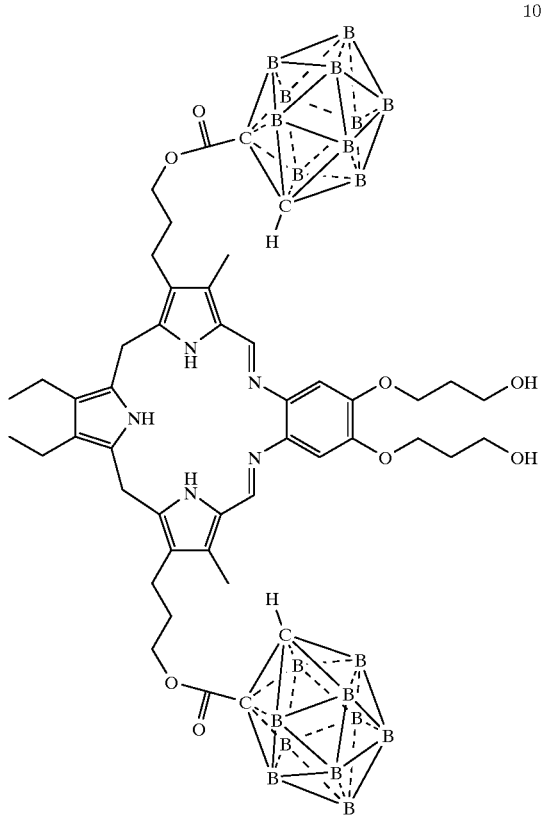

EXAMPLES 8–9 o-Nido-Carborane Derivatives

EXAMPLE 8

The gadolinium(III) bis(carborane)T2B2 texaphyrin 7b (100 mg) was added to 25 mL of piperidine-pyridine (1:4, v:v) at RT, and the reaction mixture was allowed to stand for 30 h. The solvents were evaporated off to afford the crude paroduct, which was washed several times with diethyl ether to remove any remaining amines. The solid was recrystallized from methanol-THF (1:5, v:v) to give 85 mg of the corresponding bis (o-nido-carborane) texaphyrin derivative 7c.

Alternatively, the bis(o-nido-carborane) texaphyrin derivative 7c was prepared by reacting the bis(carborane) derivative 7b (20 mg) with piperidine (1 mL) in DMF (5 mL) at 50° C. for 8h. Evaporation of the solvents, ether wash and recrystallization were done as above to give 50 mg of 7c.

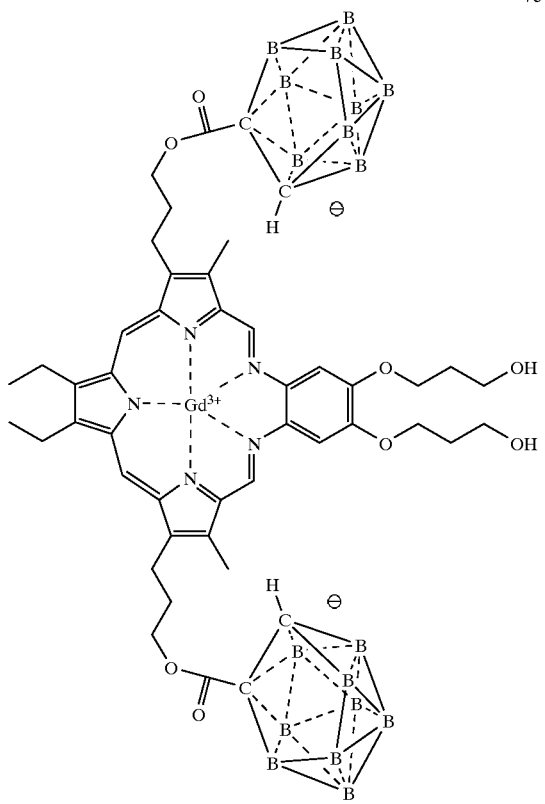

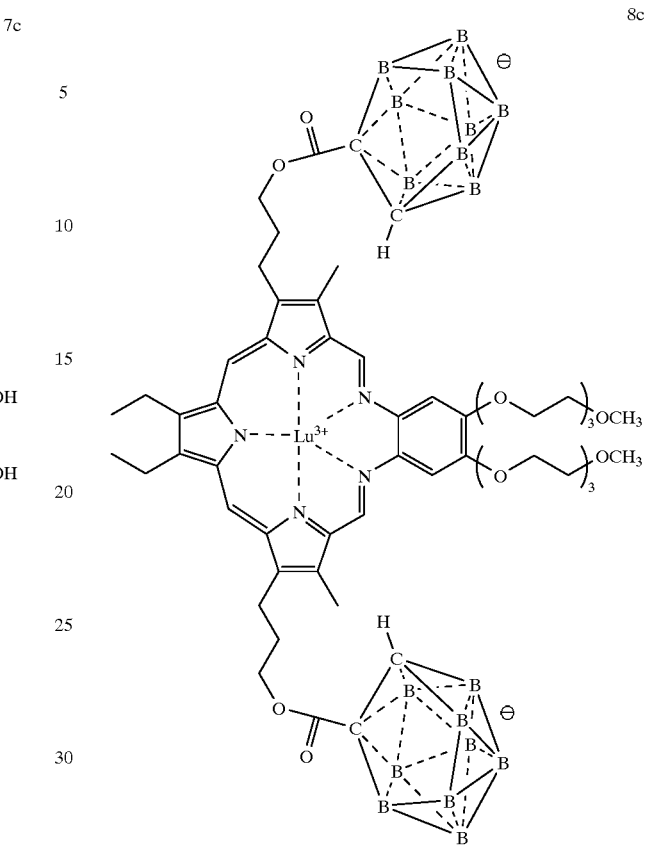

EXAMPLE 9

Following the procedures in Example 8, the Lu(III)-bis(o-nido)carborane derivative 8c was prepared from the corresponding bis(carborane)T2BET texaphyrin 8b [where M=Lu(III)].

In the same manner, the Gd(III) bis(o-nido-carborane) T2BET texaphyrin derivative corresponding to 8c (where Lu is replaced by Gd as the metal ion) was prepared following each of the above-described procedures.

EXAMPLE 10

Hydroxyalkyl- and Bromoalkyl-Substituted Tripyrrane Intermediates

Benzyl 3-methyl-5-acetoxymethyl-4-[2'-(methoxycarbonyl)ethyl]pyrrole-2-carboxylate and dibenzyl 3,3'-bis[2'-(methoxycarbonyl)ethyl]-4-4'-dimethyldipyrromethane-5,5'-dicarboxylate were prepared according to published procedures Johnson et al., *J. Chem. Soc.*, 1959, 3416–3424).

Dibenzyl 3,3'-bis(3'-hydroxypropyl)-4,4'-dimethyldipyrromethane-5,5'-dicarboxylate: A 500 mL round-bottomed flask containing a magnetic stirring bar was dried in an oven, then allowed to cool to RT under Ar. To the flask was added dimethyl ester dibenzyl ester dipyrromethane (15.0 g, 24.4 mmol). The flask was evacuated for 20 min, then 100 mL of dry tetrahydrofuran was added. The starting material dissolved with stirring to yield a light brown solution. The flask was lowered into a RT water bath, and a solution of borane (1 M in tetrahydrofuran; 100 mL, 100 mmol) was transferred to the flask over the course of 10 min, causing the brown color to be discharged. After 90 min, the reaction was quenched by careful dropwise addition of methanol until the evolution of $H_2$ had ceased. The solvents were removed on a rotary evaporator, and the resultant clear yellow oil was taken up in 150 mL of dichloromethane. The organic layer was washed twice with 0.5 M aq. HCl (400 mL total) and dried over anhydrous potassium carbonate. Filtration and evaporation of the filtrate afforded a light yellow oil which solidified upon standing under vacuum. The yield of off-white product was 12.9 g (95%). $^1$H NMR (CDCl$_3$): 1.69 (2H, br s), 1.78 (4H, quintet), 2.26 (6H, s), 2.66 (4H, t), 3.52 (4H, t), 3.79 (2H, s), 5.23 (4H, s), 7.3–7.5 (10H, m), 10.24 (2H, br s).

Dibenzyl 3,3'-bis(3'-bromopropyl)-4,4'-dimethyldipyrromethane-5,5'-dicarboxylate: Freshly crystallized (MeOH) and dried triphenylphosphine (12.8 g, 48.8 mmol) was placed in a 250 mL round-bottomed flask containing a magnetic stirring bar. A solution of diol dibenzyl ester dipyrromethane (12.4 g, 22.2 mmol) in 35 mL of dry N,N-dimethylformamide was transferred to the flask, and the contents were stirred under Ar until the triphenylphosphine had dissolved. An addition funnel containing ca. 3 mL of bromine was affixed to the flask, and very slow dropwise addition of the bromine was commenced. The temperature of the reaction was maintained below 30° C. by use of a cool water bath. Addition of 2.6 mL of bromine caused the reaction mixture to acquire a persistent, deep red color; the flask was wrapped in aluminum foil and stirring was continued for 48 h under Ar. Water (150 mL) was added, and the aqueous mixture was extracted with benzene (3 portions of 200 mL each). The organic extracts were washed with saturated aqueous sodium bicarbonate and dried over anhydrous sodium sulfate. Filtration and evaporation of the solvent afforded a dark oil which was purified by flash column chromatography using dichloromethane-ethyl acetate (99:1, v:v) as the eluent. The product was obtained as an orange-red oil which solidified upon standing. The yield was 9.7 g (64%). $^1$H NMR (CDCl$_3$): 1.93 (4H, quintet), 2.27 (6H, s), 2.59 (4H, t), 3.38 (4H, t), 3.89 (2H, s), 5.20 (4H, s), 7.2–7.5 (10H, m), 9.78 (2H, br s). LR MS (CI): 682.

3,3'-Bis(3'-bromopropyl)-4,4'-dimethyldipyrromethane-5,5'-dicarboxylic acid: A 100 mL round-bottomed flask containing the diester obtained above (1.63 g, 2.34 mmol) was charged with 60 mL of dry tetrahydrofuran and 2 drops of triethylamine. A catalytic amount of 10% palladium on activated carbon was added, and the flask was momentarily placed under vacuum. A balloon of hydrogen was affixed to the evacuated flask, the hydrogen was released, and the contents were stirred at RT in the dark until all of the starting diester had been consumed (as judged by thin layer chromatography). The reaction mixture was filtered through a pad of Celite, and the light yellow filtrate was reduced in volume using a rotary evaporator. The residue was dried under vacuum to afford 1.15 g (97%) of product, which was used immediately without further purification.

2,5-Bis[(5-(benzyloxycarbonyl)-3-[2'-(methoxycarbonyl) ethyl]-4-methylpyrrol-2-yl) methyl]-3-(3'-bromopropyl)-4-methylpyrrole (5a): Freshly prepared dibromide diacid (above) (1.15 g, 2.29 mmol) and benzyl 3-methyl-5-acetoxymethyl-4-[2'-(methoxycarbonyl) ethyl]pyrrole-2-carboxylate (1.68 g, 4.50 mmol) were combined in 30 mL of methanol. Trifluoroacetic acid (2.6 g, 23 mmol) and p-toluenesulfonic acid monohydrate (88 mg, 0.46 mmol) were added, and the contents heated to reflux in the dark under an atmosphere of Ar. After 2 h, the dark red-brown reaction mixture was allowed cool to RT, and the volatile components were removed using a rotary evaporator. The residue was purified by flash column chromatography using dichloromethane-ethyl acetate (95:5, v:v) as the eluent. After discarding several fast-moving byproducts, fractions containing the desired product were combined and chromatographed a second time using dichloromethane-ethyl acetate (90:10, v:v). A total of 0.33 g (18%) of the tripyrrane was obtained as a red-orange oil. $^1$H NMR (CDCl$_3$): 2.04 (3H, s), 2.20 (3H, s), 2.24 (3H, s), 2.2–2.4 (m), 2.5–2.7 (m), 3.4–3.6 (m), 3.43 (2H, t), 3.61 (6H, s), 4.38, (2H, br s), 4.41 (2H, br s), 6.98 (2H, s), 7.00 (2H, s), 7.1–7.5 (10H, m), 8.86 (1H, br s), 10.93, (1H, s), 11.04 (1H, s). LR MS (FAB): 828; HR MS (FAB): calcd for $C_{44}H_{50}N_3O_3Br$ 829.276081, found 829.273808.

2,5-Bis[(5-(benzyloxycarbonyl)-3-[2'-(methoxycarbonyl) ethyl]-4-methylpyrrol-2-yl)methyl]-3-(3'-hydroxypropyl)-4-methylpyrrole: Freshly prepared 3,3'-bis(3'-hydroxypropyl)-4,4'-dimethyldipyrromethane-5,5'-dicarboxylic acid (1.8 g, 4.8 mmol) (from hydrogenation of dibenzyl 3,3'-bis(3'-hydroxypropyl)-4,4'-dimethyldipyrromethane-5,5'-dicarboxylate over Pd/C) and benzyl 3-methyl-5-acetoxymethyl-4-[2'-(methoxycarbonyl)-ethyl]pyrrole-2-carboxylate (3.5 g, 9.5 mmol) were combined in 30 mL of methanol. Trifluoroacetic acid (5.5 g, 48 mmol) and p-toluenesulfonic acid monohydrate (0.18 g, 0.96 mmol) were added, and the contents heated to reflux in the dark under an atmosphere of Ar. After 2 h, the brown-black reaction mixture was allowed cool to rt, and approximately one-fourth of the volatile components were removed using a rotary evaporator. The heterogeneous mixture which remained was tightly capped and placed in a freezer overnight. The precipitate was collected by filtration and washed with ice-cold methanol to afford the product as a rust-colored solid. LR MS (FAB): 765; HR MS (FAB): calcd for $C_4H_{50}N_3O_9$ 764.354706, found 764.353893.

What is claimed is:

1. A highly boronated derivative of a texaphyrin having the following formula A:

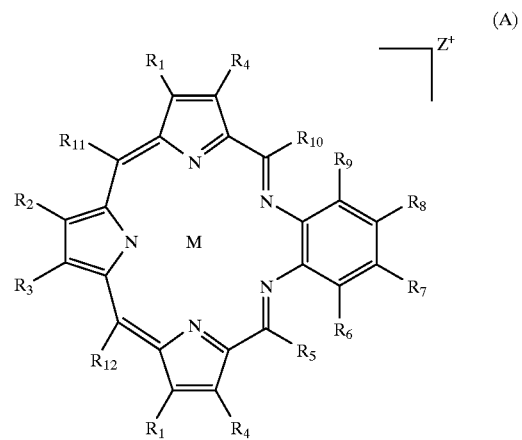

wherein,

M is a divalent metal cation or a trivalent metal cation;

each of $R_1$–$R_4$, and $R_6$–$R_9$ is independently selected from the group consisting of hydrogen, halide other than iodide, hydroxyl, alkyl, alkenyl, aryl, haloalkyl other than iodoalkyl, nitro, formyl, acyl, hydroxyalkyl, oxyalkyl, oxyhydroxyalkyl, saccharide, aminoalkyl, oxyaminoalkyl, carboxy, carboxyalkyl, carboxyamidealkyl, carboranyl, a catalytic group, and a site-directing molecule selected from the group consisting of a polynucleotide, and oligonucleotide, a peptide having affinity for a biological receptor, a protein, a steroid, a hormone, a hormone mimic, a sapphyrin and a rubyrin; with the proviso that at least one of $R_1$–$R_4$ and $R_6$–$R_9$ is carboranyl;

each of $R_5$ and $R_{10-R_{12}}$ is independently selected from the group consisting of hydrogen, alkyl, alkenyl, aryl, hydroxyalkyl, oxyalkyl, oxyhydroxyalkyl, aminoalkyl, oxyaminoalkyl, carboxyalkyl, and carboxyamidealkyl; and Z is zero or an integer less than or equal to 5.

2. A highly boronated derivative of texaphyrin according to claim 1 wherein the site-directing molecule is an oligonucleotide.

3. A highly boronated derivative of texaphyrin according to claim 1 wherein M is a metal cation selected from the group consisting of Mn(II), Mn(III), Fe(III), Y(III), and all trivalent lanthanides other than La(III), Lu(III) and Pm(III).

4. A highly boronated derivative of a texaphyrin according to claim 1 wherein $R_1$ is carboranyl; each of $R_2$, $R_3$ and $R_4$ is alkyl; each of $R_7$ and $R_8$ is independently selected from the group consisting of hydrogen, alkyl, hydroxyalkyl, oxyalkyl, oxyhydroxyalkyl, and a site-directing molecule; and, $R_5$, $R_6$ and $R_9$–$R_{12}$ are hydrogen.

5. A highly boronated derivative of a texaphyrin according to claim 1 wherein $R_1$ is carboranyl; each of $R_2$ and $R_3$ is ethyl; $R_4$ is methyl; $R_7$ and $R_8$ are selected from hydroxypropoxy and the group —O(CH$_2$CH$_2$O)$_x$CH$_3$, where x=1–100; and, $R_5$, $R_6$ and $R_9$–$R_{12}$ are hydrogen.

6. A highly boronated derivative of a texaphyrin according to claim 5 wherein x=1–10.

7. A highly boronated derivative of a texaphyrin according to claim 4 wherein M is selected from Y(III), Lu(III), Gd(III), Eu(III), Dy(III) and Tb(III).

8. A highly boronated derivative of a texaphyrin according to claim 5 wherein M is selected from Y(III), Lu(III), Gd(III), Eu(III), Dy(III) and Tb(III).

9. A highly boronated derivative of a texaphyrin according to claim 1 wherein at least one of $R_1$, $R_7$ and $R_8$ is carboranyl.

10. A highly boronated derivative of a texaphyrin according to claim 1 wherein at least one of $R_1$, $R_7$ and $R_8$ is carboranyl; and the others of $R_1$, $R_7$ and $R_8$ are independently selected from the group consisting of hydrogen, alkyl, hydroxyalkyl, oxyalkyl, oxyhydroxyalkyl, and a site-directing molecule.

11. A highly boronated derivative of a texaphyrin according to claim 10 wherein each of $R_2$, $R_3$ and $R_4$ is alkyl; and, $R_5$, $R_6$ and $R_9$–$R_{12}$ are hydrogen.

12. A highly boronated derivative of a texaphyrin according to claim 1 wherein at least one of $R_2$ and $R_3$ is carboranyl.

13. A highly boronated derivative of a texaphyrin according to claim 1 wherein one of $R_7$ and $R_8$ is carboranyl; and the other of $R_7$ and $R_8$ is selected from the group consisting of hydrogen, alkyl, oxyalkyl, and oxyhydroxyalkyl.

14. A highly boronated derivative of a texaphyrin according to claim 1 wherein the carboranyl comprises a carboranyl cluster and a linking moiety.

15. A highly boronated derivative of a texaphyrin according to claim 5 wherein the carboranyl comprises a carboranyl cluster and a linking moiety.

16. A highly boronated derivative of a texaphyrin according to claim 8 wherein the carboranyl comprises a carboranyl cluster and a linking moiety.

17. A highly boronated derivative of a texaphyrin according to claim 11 wherein the carboranyl comprises a carboranyl cluster and a linking moiety.

* * * * *